US008876664B2

(12) United States Patent
Bell et al.

(10) Patent No.: US 8,876,664 B2
(45) Date of Patent: Nov. 4, 2014

(54) WEIGHT-LIFTING EXERCISE MACHINE

(71) Applicant: Edward J. Bell, Medford, NJ (US)

(72) Inventors: Edward J. Bell, Medford, NJ (US); Igor Grinko, Augusta, GA (US); Seamus Woods, Brewster, MA (US)

(73) Assignee: Edward J. Bell, Medford, NJ (US)

( * ) Notice: Subject to any disclaimer, the term of this patent is extended or adjusted under 35 U.S.C. 154(b) by 0 days.

(21) Appl. No.: 13/965,834

(22) Filed: Aug. 13, 2013

(65) Prior Publication Data
US 2014/0024497 A1    Jan. 23, 2014

Related U.S. Application Data

(62) Division of application No. 12/907,807, filed on Oct. 19, 2010, now Pat. No. 8,529,408.

(51) Int. Cl.
A63B 24/00    (2006.01)

(52) U.S. Cl.
USPC ........... 482/8; 482/1; 482/3; 482/93; 482/900

(58) Field of Classification Search
USPC ................. 482/1–9, 142, 148, 900–902, 93; 434/247; 600/595
See application file for complete search history.

(56) References Cited

U.S. PATENT DOCUMENTS

| 4,691,916 | A | | 9/1987 | Voris |
| 4,720,103 | A | | 1/1988 | Palladino |
| 4,743,011 | A | | 5/1988 | Coffey |
| 5,271,416 | A | * | 12/1993 | Lepley .......................... 600/595 |
| 5,476,428 | A | * | 12/1995 | Potash et al. ...................... 482/5 |
| 6,146,312 | A | * | 11/2000 | Sclichter .......................... 482/4 |
| 6,537,182 | B2 | | 3/2003 | Slawinski |
| 6,592,498 | B1 | | 7/2003 | Trainor |
| 6,790,163 | B1 | | 9/2004 | Van De Laarschot |
| 7,104,936 | B2 | | 9/2006 | Karlstrom |
| 7,258,653 | B2 | * | 8/2007 | Brandon et al. ............. 482/142 |
| 7,771,318 | B2 | * | 8/2010 | Narayanaswami ............... 482/8 |
| 7,789,812 | B2 | | 9/2010 | Anderson |
| 7,998,038 | B2 | | 8/2011 | Keiser |
| 8,638,228 | B2 | * | 1/2014 | Amigo et al. .............. 340/573.1 |
| 2007/0219059 | A1 | * | 9/2007 | Schwartz et al. ................ 482/8 |
| 2008/0242512 | A1 | | 10/2008 | Kim |
| 2010/0227738 | A1 | * | 9/2010 | Henderson ........................ 482/8 |

* cited by examiner

Primary Examiner — Glenn Richman
(74) Attorney, Agent, or Firm — William H. Eilberg

(57) ABSTRACT

A weight-lifting exercise machine enables an athlete to lift a mass from an initial resting position. After the athlete releases the mass, the machine cushions the fall of the mass, such that the mass returns to its resting position without assistance from the athlete. The movements of the athlete and the mass can be tracked, preferably by wireless accelerometers attached respectively to the athlete and the mass, and data on such movements can be stored and analyzed. The machine provides a monitor to enable the athlete to track the progress of the exercise, and to determine whether the exercise is being performed correctly.

6 Claims, 19 Drawing Sheets

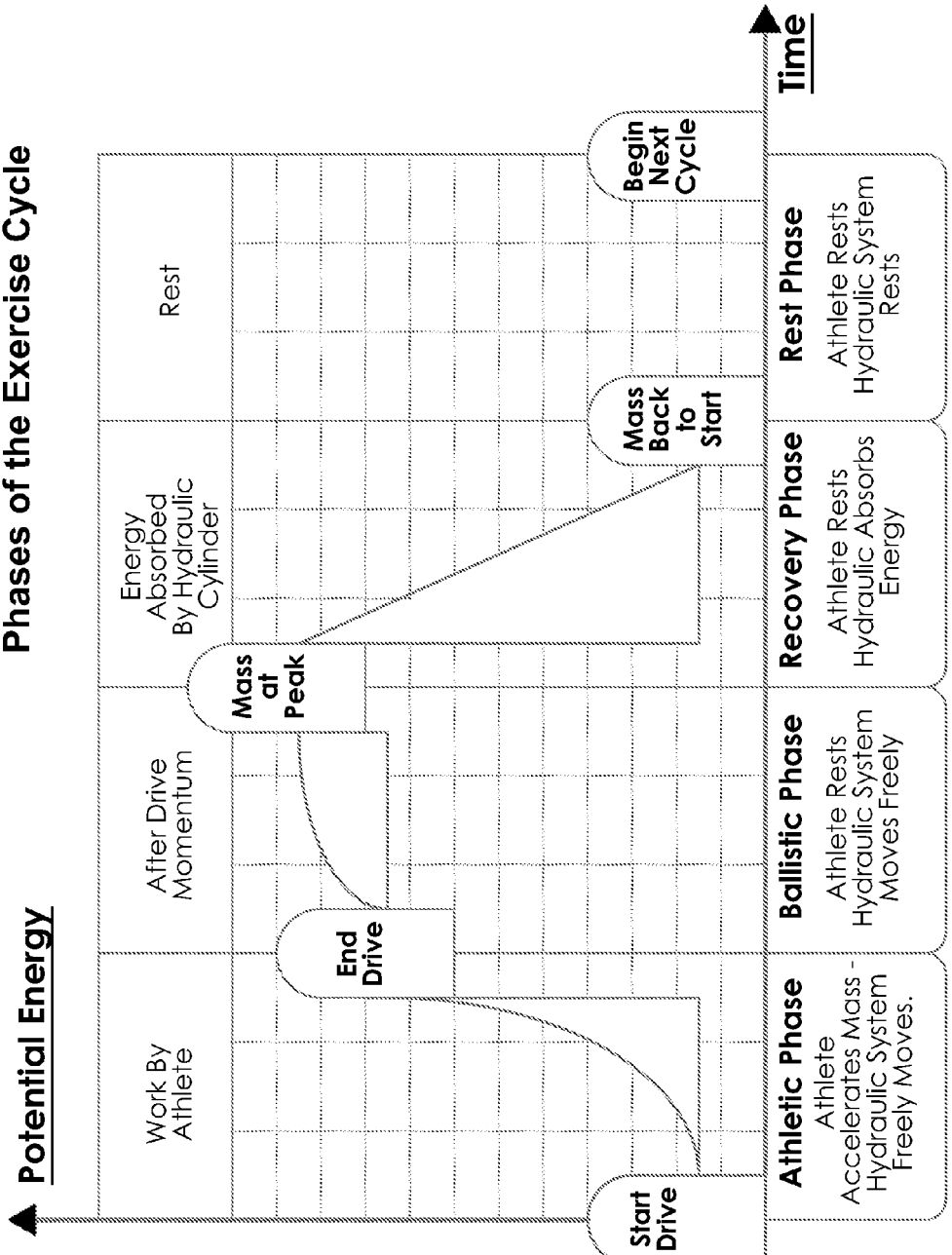

Monitor Software Sensor Processing & Display Flow Chart

Facility
Data Processing
FLow Chart

FIG 19.

| Parameter | Description | How Calculated | Accumulated | Trended - Graphed |
|---|---|---|---|---|
| XMax | Maximum Height of the Mass During a Lift | Max Value of VMass x Time | Yes | Yes |
| XDrive | Height of Mass when A=0 | Value of VMass x Time at A=0 | Yes | Yes |
| XBallistic | Mass Travel after XDrive | XMax-XDrive | Yes | Yes |
| VMax | Maximum Velocity of the Mass During a Lift | Max Value of AMass x Time | No | Yes |
| AMax | Maximum Value of AMass during a single Lift | Max Value of AMass during a single Lift | No | Yes |
| V@XDrive | Velocity at the end of the Atletic Effort | Value of VMass at A=0 | No | Yes |
| Count | Lift Count, Each Lift Starts from Mass at Rest | Each Lift is One Integer Value | Yes | No |
| Lifts per Minute | Frequency of Lift | 60/ Time Betwen Strokes | No | Yes |
| Drive Ratio | Normalized Value of Acceleration Coordination | (Time to XMax)/((Time to XMax)/2) | No | Yes |
| Core Departure Point | Distance in Mass Height Where the Mass is moving Faster than the Core | Write XMax when VCore=VMass x .99 [ACore x time = VCore] | No | Yes |
| Local Max | Point, if any, of a local Max in VMass | Return XMass where iteration of VMass(n)-Vmass(n+)<0, N is based on the data sample rate | No | Yes |

WEIGHT-LIFTING EXERCISE MACHINE

CROSS-REFERENCE TO PRIOR APPLICATION

This is a division of U.S. patent application Ser. No. 12/907,807, filed Oct. 19, 2010.

BACKGROUND OF THE INVENTION

The present invention relates generally to the field of weight-lifting exercise equipment where the weight is accelerated by the athlete during an entire lifting motion.

There are many types of weight-lifting exercise machines, and these devices vary in complexity. One of the simplest forms of such devices is a free weight, where the device is a mass with some means of gripping, and the user lifts the weight by the grips. More complex lifting equipment includes levers, pulleys, selectable weights, and/or spotting systems. In all of these cases, the stroke of the exercise occurs where the user moves a mass against gravity, using personal muscular effort.

There are many training regimens that prescribe frequency of lift, weight progression, technique of lifting etc. These regimens typically require that a mass start at a point, and that it return to the same point through one cycle of the exercise technique. This cycle defines the range of motion through which the mass should travel. The purpose of the exercise is to build strength and endurance.

The exercise devices of the prior art facilitate the user's effort while moving the mass against gravity, but they also require the user to expend effort to bring the mass back to its starting point. In addition, recording the workout has traditionally been done by hand, by writing down the pertinent data, such as mass lifted and the number of repetitions.

An exercise machine, built by the present inventor in 1996, included a mass which was accelerated upwardly against gravity by the user. A flywheel system returned the mass to its starting point. A cable system transferred the potential energy of the mass into the flywheel, and the flywheel was connected to a fan which dissipated the energy by air resistance. This system worked, but had the major disadvantage that the mass would continue to accelerate downwardly, albeit at a slower rate, requiring the user to prevent the mass from slamming into the stationary portion of the machine. Also, the device included no automatic means for monitoring the progress of the exercise.

U.S. Pat. No. 7,104,936 (Karlstrom) discloses an exercise machine which allows the user to lift a mass upward, and wherein a cylinder returns the mass to its starting point by throttling hydraulic fluid through a metering orifice. This system is useful in the applications illustrated in the patent, but lacks the ability to be used with horizontal motions, complex multi-muscle group motions such as the rowing stroke, and various mechanized lifting motions such as leg extensions.

The present invention comprises a substantial improvement over the prior art, insofar as it includes a weight-lifting machine in which a mass is automatically returned to its resting position, without the aid of the athlete. The device of the present invention also includes features which facilitate the monitoring of progress of the athlete, and the recording of relevant data. The device also provides immediate feedback to the athlete, and can signal the athlete when the exercise is not being performed correctly.

SUMMARY OF THE INVENTION

In the exercise machine of the present invention, a frame supports a movable mass, which is connected to cables which are in turn connected to a hydraulic cylinder. The hydraulic cylinder is configured to operate in one direction freely, but in a restricted manner in the opposite direction. The restriction is provided by metering hydraulic fluid through a metering valve, or by other equivalent means. The user, through a separate cabling system, extends the cable to lift the mass.

The exercise machine of the present invention allows the mass to have a large range of motion. In particular, the machine is intended to allow the mass to have upward velocity after the athlete is no longer applying upward force to lift the mass.

The machine also includes a recovery system which does not require the user to catch the downwardly accelerating mass. Because the machine automatically catches the mass, the user does not need to divert his or her attention from performing the lifting action properly, or to expend workout energy in re-setting the mass. Moreover, the recovery system protects the machine frame and the mass from high impact forces.

In order to analyze the performance of the athlete, a monitor and logging system is also provided. This system includes accelerometers connected to the mass and to the athlete. The accelerometers are preferably connected wirelessly to a computer or equivalent device. Other monitoring devices could include a heart rate monitor, a clock, and a rotary encoder.

The above-described sensors send performance data to the machine monitor for immediate feedback to the user. The data feedback is vital to train the user to know what application achieves the right motion for the right sport. Moreover, the data from such sensors can be appended to a database, allowing for analysis of trends over time, i.e. to track the progress of an athlete. Such data can also be used for comparison of the performance of one athlete with another. The data may be transmitted to a web server, allowing the system to be used by different persons in multiple locations.

The present invention therefore has the primary object of providing a weight-lifting exercise machine.

The invention has the further object of providing an exercise machine in which an athlete is required to lift a weight, and in which the weight is returned to its starting position without assistance from the athlete.

The invention has the further object of providing a weight-lifting exercise machine, in which the machine is protected from damage by means for damping the fall of a mass back to its starting position.

The invention has the further object of providing an exercise machine which measures and tracks the progress of an athlete, and provides feedback concerning the motions exerted by the athlete.

The invention has the further object of providing an exercise machine which can analyze data on the performance of an athlete in real-time, and which can signal to the athlete that an exercise is not being performed correctly.

The reader skilled in the art will recognize other objects and advantages of the present invention, from a reading of the following brief description of the drawings, the detailed description of the invention, and the appended claims.

BRIEF DESCRIPTION OF THE DRAWINGS

FIG. 4 provides a graph which illustrates the phases of the athletic and mechanical cycle of the machine of the present invention.

FIG. 19 provides a table illustrating and describing various exercise parameters used in the present invention.

DETAILED DESCRIPTION OF THE INVENTION

Figure 1:
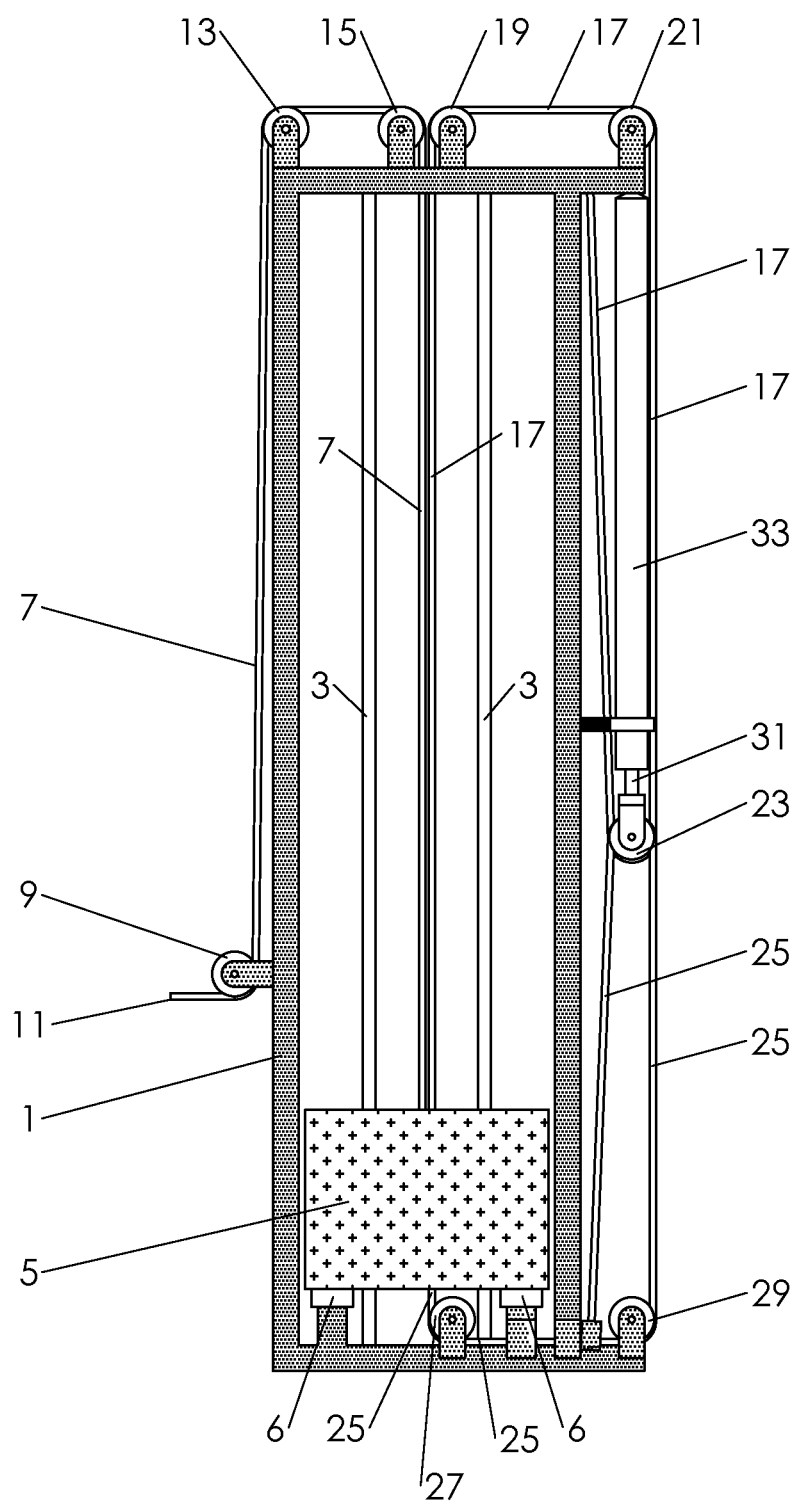
FIG. 1 provides a side elevational view of the exercise machine of the present invention, illustrating the machine in its resting position, i.e. with the mass at its lowest point.

The present invention relates to weight-lifting exercise equipment that allows the user to accelerate a mass against gravity, throughout the entire motion of an exercise cycle, and wherein the user intends that the mass continue to move, against the force of gravity, after the user has completed the motion. The mass is then caught by a cabling system which is connected to a hydraulic system, or its equivalent, which restores the mass to its original position.

One purpose of the machine of the present invention is to develop the user's ability to provide power through the entire time during which the mass is lifted. When an athlete moves the mass in this manner, the mass will have a non-zero velocity at the moment the athlete has completed the motion.

If the above-described motion were to be done with equipment of the prior art, the mass would simply continue upward, then reverse direction, and then accelerate downward. The greater the achieved velocity at the completion of the motion, the higher the velocity when the user would then need to retard the mass and reset the mass to the starting point.

In the above-described scenario, the athlete would be vulnerable to injury due to the need for repetitive high-impact catching of the mass. Due to the energy spent on such recovery, the athlete could be expected to reduce the number of repetitions of the exercise cycle. Moreover, the athlete using a prior art machine is likely to contort the desired motion of acceleration during the lift, in anticipation of having to catch the mass when it falls back.

The present invention reduces or eliminates the above problems, making it much easier for an athlete to perform multiple repetitions of an exercise cycle, and to exercise multiple muscle groups.

When accelerated lifting is done by multiple muscle groups, these muscle groups become trained to activate sequentially, starting with the larger muscle groups and adding smaller muscle groups throughout the progress of the exercise. This training occurs with multiple repetitions, and with a mass large enough that it cannot be lifted by the smaller muscle groups alone. By performing this exercise a multiplicity of times, the user derives substantial benefits. The machine of the present invention makes it possible to perform workouts which include as many as 400 repetitions of lifting a mass which is greater than the athlete's body weight, in exercises that use two or more major muscle groups.

The machine of the present invention has a user side and a recovery side. The user side links the mass to the athlete. This linking is achieved by a cable that is connected to an existing lifting mechanism, such as a handle. The recovery side comprises a system including cables, pulleys, and a single-direction hydraulic cylinder. The recovery cabling system transfers the energy of the mass at the catch point so that the mass safely descends to the starting point of the exercise. The cabling system can be configured to compound, if needed, to multiply the range of motion of the exercise.

The primary means of energy absorption, in the machine of the present invention, is a single-acting hydraulic cylinder which receives energy via a cable and pulleys from the mass. The cylinder operates in one direction using a small fraction of user effort. When the mass reverses direction from opposing gravity, the cylinder resists force by metering hydraulic fluid through an adjustable valve.

In the present specification, the terms "user" and "athlete" are used interchangeably to mean the person using the exercise machine of the present invention.

FIG. 1 shows the exercise machine of the present invention, with the mass in a resting position. The left-hand side of the machine is the user side, and the right-hand side in the figure is the recovery side. Frame 1 supports tracks or rails 3 along which mass 5 can freely slide up or down. The mass sits on supports 6. First cord 7 passes around pulley 9 and defines a terminus 11 which can be grasped by the athlete. In practice, the terminus of the cord could be connected to a handle or other device which can more easily be gripped. The first cord 7 passes over pulleys 13 and 15, at the top of the machine, and extends downwardly, and is connected to mass 5. Thus, when the athlete pulls on first cord 7, the mass tends to be pulled upward.

The right-hand side, or recovery side, of the machine of the present invention uses two cords (designated the second and third cords of the machine). Second cord 17, like first cord 7, is also connected to mass 5. The second cord 17 passes around pulleys 19 and 21, then around one of a pair of pulleys 23, and then passes upwardly where it is anchored to the frame near pulley 21. Third cord 25 is connected to the bottom of mass 5, and passes around pulleys 27 and 29, then around the other of the pair of pulleys 23, and then passes downwardly where it is anchored to the frame near pulley 29.

Pulleys 23 comprise two, side-by-side pulleys. One of these pulleys is obscured in the elevational views, such as FIG. 1, but the presence of a pair of pulleys is indicated in the perspective view of FIG. 15. Thus, the second and third cords, described above, can be wound around different pulleys of the pair, so that the cords do not interfere with each other. The pulleys 23 otherwise move together.

Pulleys 23 are connected to a piston 31 which, together with cylinder 33, forms part of a piston and cylinder assembly. The piston can slide back and forth within the cylinder. That is, the piston can extend or retract relative to the cylinder. As will be explained in more detail later, the piston and cylinder assembly is designed such that one of the extension and retraction motions is restricted, and the opposite motion is substantially unrestricted. In the specific example represented by FIG. 1, the extension is substantially unrestricted, and the retraction is restricted.

Figure 2:
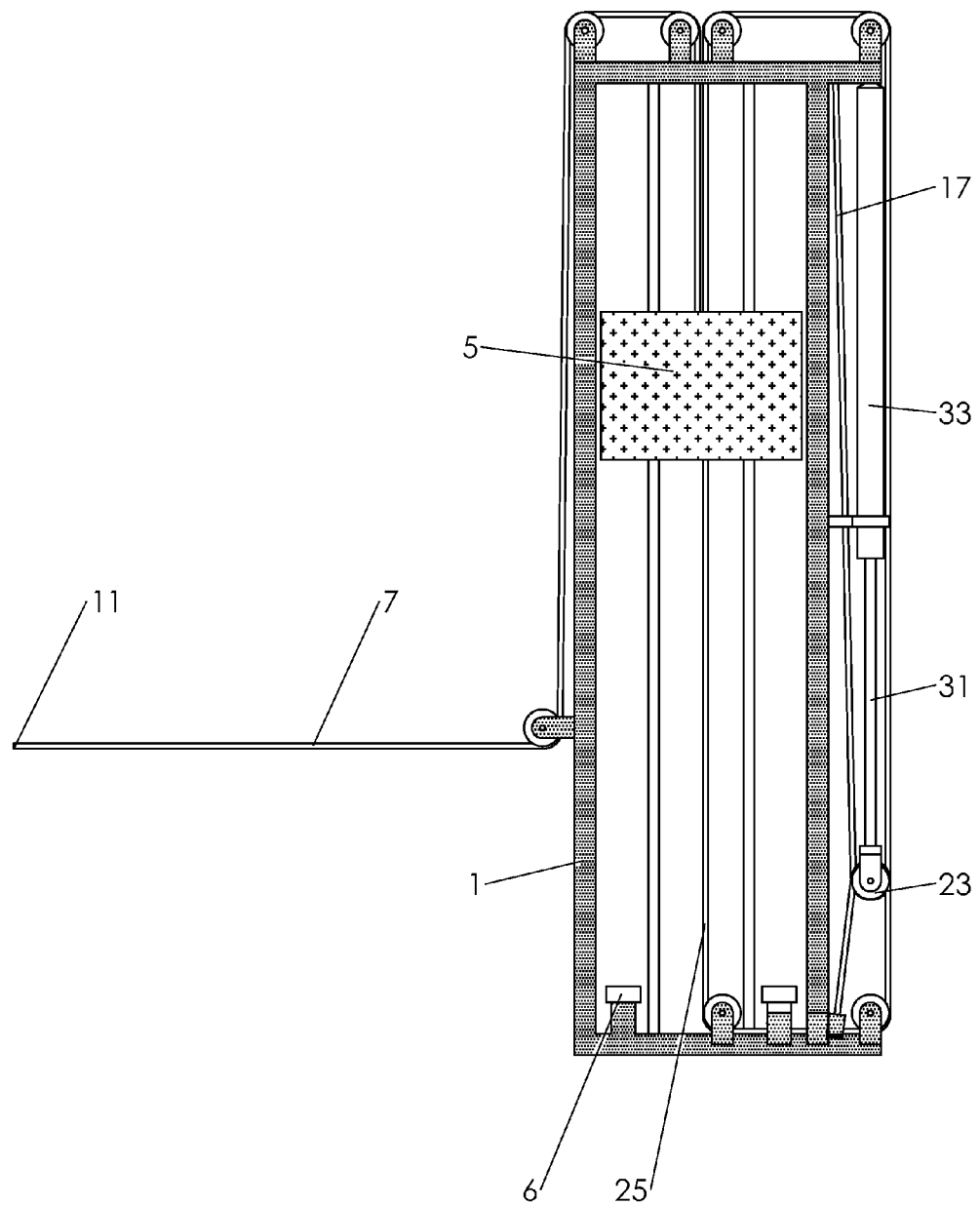
FIG. 2 provides a side elevational view of the exercise machine of the present invention, showing the mass at about the point at which the athlete has released the cable connected to lift the mass, and wherein the mass is still moving upward due to the energy imparted to it.

FIG. 2 illustrates the condition of the machine of the present invention when the athlete (not shown) has pulled first cord 7, so as to accelerate mass 5 upwardly. The figure illustrates the moment at which the athlete has just released the first cord. At this moment, the mass is still moving upwardly, due to inertia. Because the mass has moved upwardly, it has pulled on third cord 25, which, because it is wound around one of the pulleys 23, exerts downward force on piston 31, due to the fact that the other end of the third cord is anchored to the frame 1. Therefore, the upward motion of the mass 5 causes piston 31 to be extended from the cylinder 33, as shown in FIG. 2. The second cord 17 is maintained in a generally taut condition, due to the downward movement of the other of pulleys 23, but does not otherwise contribute to the movements of the components.

Figure 3:
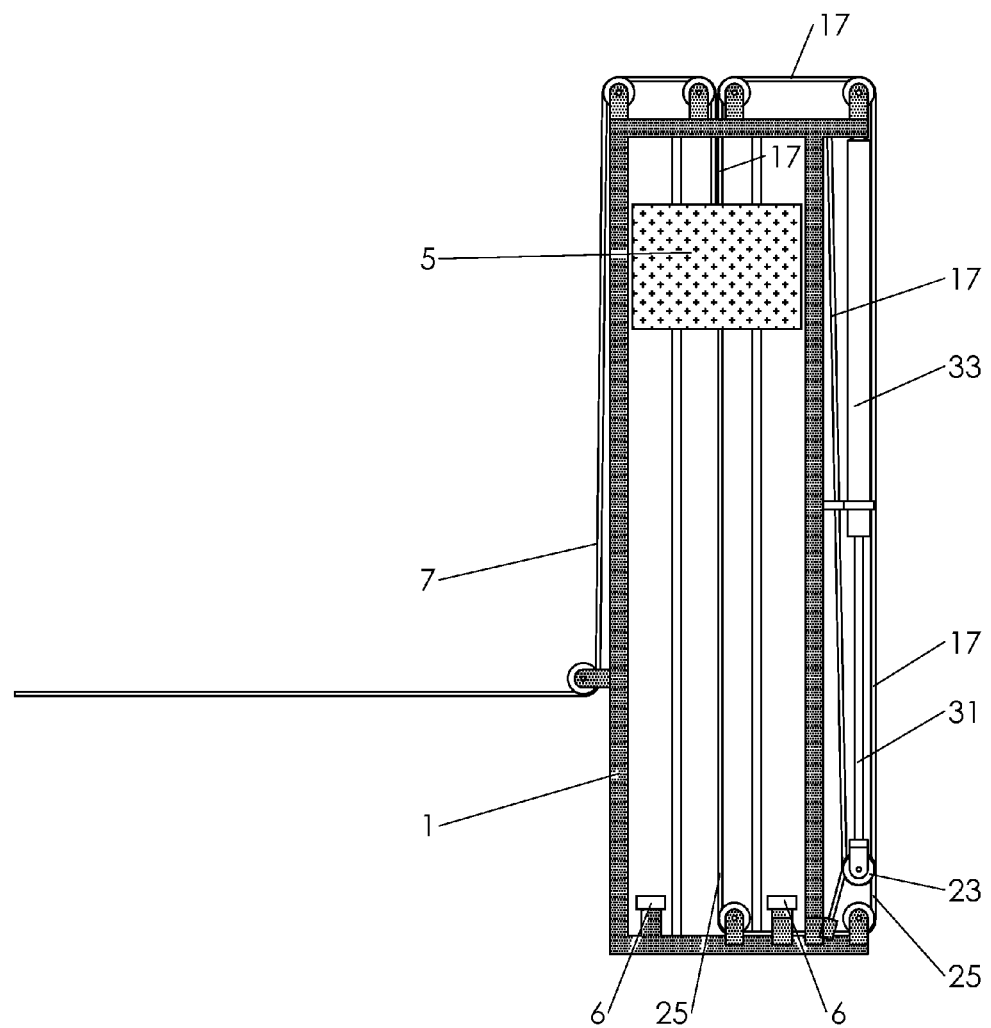
FIG. 3 provides a side elevational view of the exercise machine of the present invention, showing the mass at its highest point, when the mass is about to reverse direction and fall downward.

FIG. 3 illustrates the condition of the machine of the present invention, wherein the mass 5 is at its highest point, and is just about to reverse direction and fall downward. Note that it is assumed that, between the position shown in FIG. 2 and that shown in FIG. 3, the athlete has not been pulling first cord 7. Thus, the mass 5 has risen due to that fact that it had a non-zero upward velocity when the athlete released the cord 7. The upward movement of the mass causes the piston 31 to become fully, or nearly fully extended.

As the mass 5 falls, due to gravity, from the position shown in FIG. 3, the mass pulls on second cord 17. Because second cord 17 passes around one of pulleys 23, and because the second cord is anchored to the top portion of the frame 1, the downward movement of the mass 5 causes the piston 31 to retract, i.e. to move upward into the cylinder. However, as noted above, the piston and cylinder assembly is configured such that retraction is restricted. That is, the piston retracts into the cylinder against resistance. Therefore, the downward movement of the mass 5 is slowed, and the mass eventually will come to rest on supports 6 without excessive impact force being applied to such supports.

While the mass 5 is moving downwardly, the third cord 25 is maintained in a generally taut condition due to the upward movement of pulleys 23, which movement occurs as the piston is retracted into cylinder 33. At the same time, the first cord 7 is simply pulled by the mass, so that it eventually returns to the position shown in FIG. 1. While the mass is moving downwardly, the third cord does not significantly contribute to the motion of the components.

FIG. 4 provides a graph which illustrates the four phases of the exercise cycle, as practiced with the machine of the present invention. The vertical axis represents potential energy of the mass (proportional to the height of the mass), and the horizontal axis represents time.

The first phase of the exercise cycle is the athletic phase, i.e. the work done by the athlete. The athlete accelerates the mass, and releases the mass at a point which is short of the total height of the machine. During this phase, the hydraulic system moves freely. In the example of FIGS. 1-3, the piston extends freely from the cylinder.

The second phase of the exercise cycle is the ballistic phase, at which time the athlete rests, and the mass continues to move upward due to the fact that it has been released while moving upward. During this phase, gravity pulls against the mass, and at the end of this phase, the mass reaches its peak position, and slows to zero velocity. During this phase, the hydraulic system continues to move freely.

The third phase of the exercise cycle is the recovery phase. During this phase, the athlete still rests, while the mass falls by gravity. At this time, the energy of the mass is absorbed by the hydraulic system. In the example of FIGS. 1-3, the piston is retracted into the cylinder, but such retraction is restricted. Thus, the hydraulic system acts as a brake on the mass, and the mass falls more slowly than it otherwise would. At the end of the recovery phase, the mass has reached the bottom, i.e. the starting point.

The fourth phase of the exercise cycle is the rest phase. The athlete continues to rest during this phase, and the hydraulic system and the mass are also at rest.

Figure 5A:
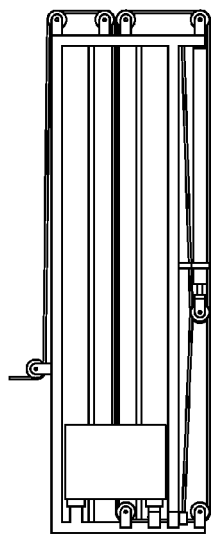
FIGS. 5a-5d provide elevational views of four phases of the machine of the present invention, illustrating the athletic and mechanical cycle thereof.
Figure 5B:
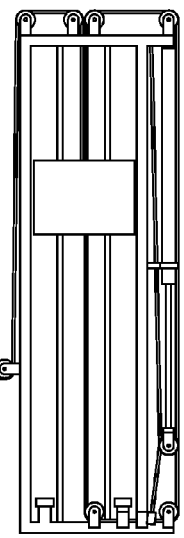
Figure 5C:
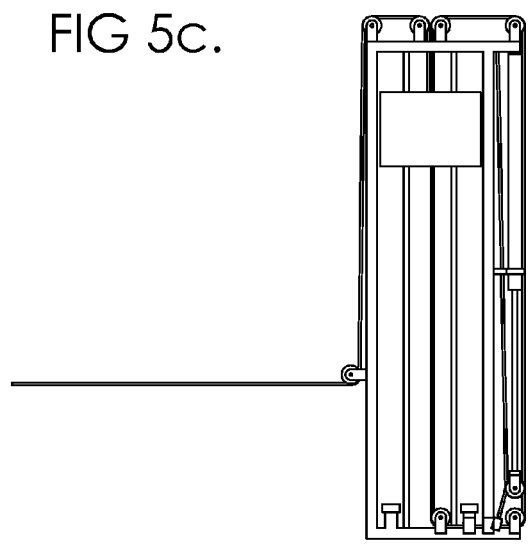
Figure 5D:
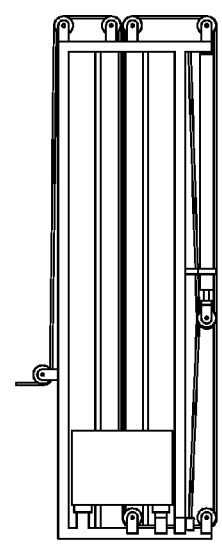

FIGS. 5a-5d summarize the four phases of the exercise cycle, showing the position of the machine in each phase. Thus, FIG. 5a shows the machine at rest. FIG. 5b shows the machine at the end of the athletic phase, i.e. the point at which the athlete has lifted the mass to the position shown, and has released the mass. FIG. 5c shows the machine at the end of the ballistic phase, wherein the mass has reached its highest point, after being released by the athlete. FIG. 5d shows the machine in the rest phase, wherein the mass has returned to its starting position.

Figure 6A:
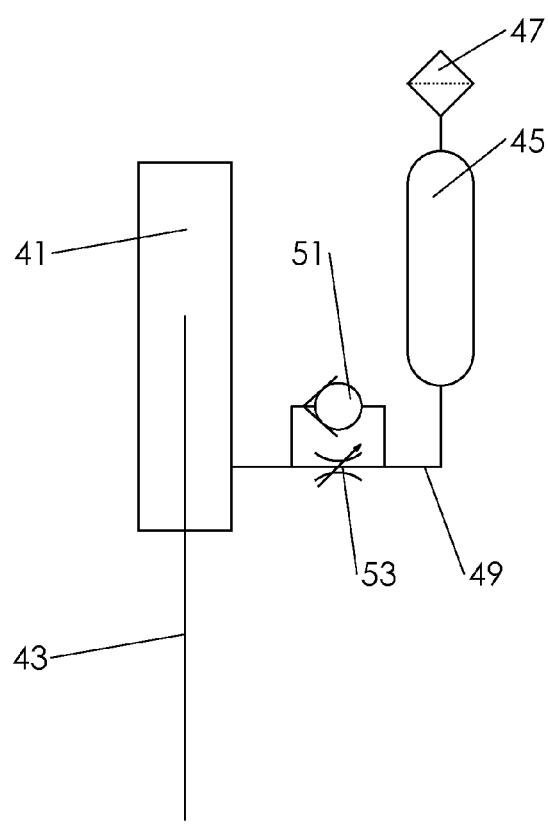
FIGS. 6a and 6b provide schematic diagrams of two embodiments of the hydraulic system used in the exercise machine of the present invention.
Figure 6B:
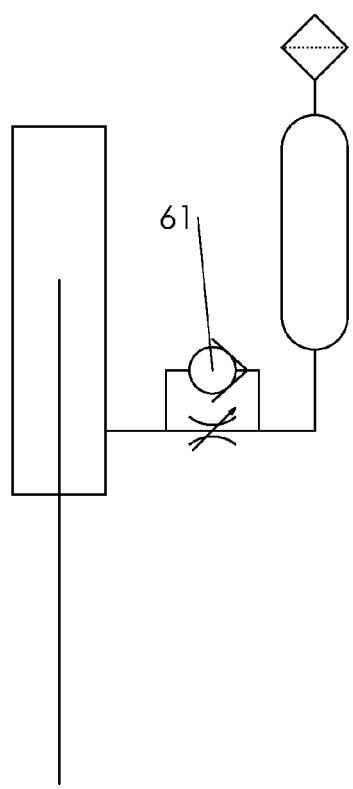

FIGS. 6a and 6b provide schematic diagrams which illustrate the operation of the hydraulic system in the present invention. In FIG. 6a, piston 43 slides back and forth within cylinder 41. Reservoir 45 stores hydraulic fluid, and a vent valve 47 allows for release of fluid in the event of overpressure. The reservoir is fluidly connected to the cylinder by conduit 49, in which there are a check valve 51 and a needle valve 53, the valves being connected in parallel.

In the arrangement of FIG. 6a, the check valve allows free flow from left to right, and blocks fluid flow from right to left. Therefore, piston 43 may retract freely, because as it does, fluid from the cylinder flows through the check valve and into the reservoir. But extension of the piston is restricted, because such extension tends to pull fluid out of the reservoir and towards the cylinder. Fluid flowing out of the reservoir cannot flow through the check valve, and instead must pass through a small orifice defined by the needle valve. The arrow on the needle valve represents a control governing the effective size of the valve orifice.

The arrangement of FIG. 6b differs from that of FIG. 6a in that the check valve 61 is connected in the opposite direction as compared with check valve 51. Thus, in the case of FIG. 6b, extension of the piston is unrestricted, because fluid can freely flow from the reservoir, through the check valve, to the cylinder. But retraction of the piston is restricted, because fluid flowing from the cylinder towards the reservoir cannot flow through check valve 61, and must pass through the small orifice of the needle valve.

FIG. 6b is thus appropriate to the arrangement shown in FIGS. 1-3, which requires a piston which extends freely, and in which retraction is restricted. The arrangement of FIG. 6a can be used in the embodiment of FIG. 7, which will be explained below.

Figure 7:
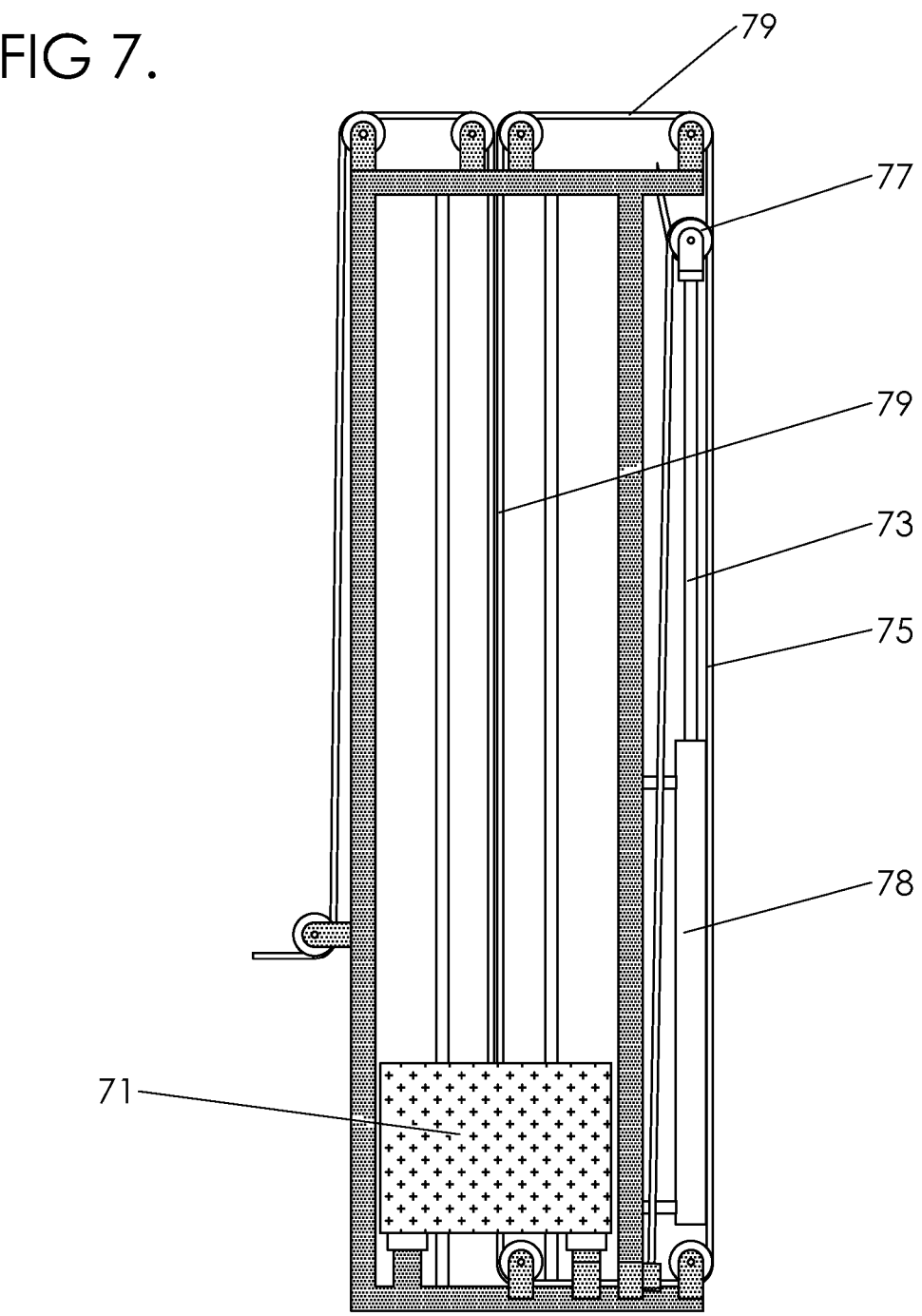
FIG. 7 provides a side elevational view of an embodiment of the present invention in which the cylinder is configured to collapse or retract freely but to extend in a restricted or metered manner, this embodiment being intended for use with especially heavy masses.

FIG. 7 illustrates an embodiment of the invention which uses the hydraulic arrangement of FIG. 6a. This embodiment is intended for the case in which the mass is especially heavy. Thus, in FIG. 7, it is assumed that mass 71 weighs much more than mass 5 of FIG. 1.

The problem with a heavy mass is that, in the embodiment of FIG. 1, it can cause damage to the piston and cylinder assembly. In FIG. 1, when the mass is falling to its position at the bottom of the frame, the piston is retracting into the cylinder. When the mass is very heavy, the mass may impose excessive forces on the piston, and may cause buckling and breakage of the piston.

The solution to the above-described problem is provided by the arrangement of FIG. 7. In this arrangement, the piston 73 is in its fully extended position when the mass is at its starting position, as shown in the figure. As the mass is lifted, the mass pulls on cord 75 which passes around one of a pair of pulleys 77 and is anchored at the bottom of the frame. Thus, as the mass is lifted, the piston is retracted into cylinder 78.

When the mass 71 is falling down, it pulls on cord 79, which pulls on the other of the pair of pulleys 77, thereby exerting force to extend the piston from the cylinder. But because the motion of extension is restricted, the movement of the mass is opposed, and its fall is cushioned.

Therefore, the piston and cylinder assembly of FIG. 7 should be constructed according to the embodiment of FIG. 6a, wherein the piston may retract freely, but where extension of the piston is restricted.

One of the important benefits of the exercise machine of the present invention is its ability to obtain and record information about the performance of the athlete, and to guide the athlete so as to improve such performance. This information is obtained by placing an accelerometer on the athlete, and on the mass being moved, and by connecting the outputs of the accelerometers to a computer or equivalent.

The accelerometer provides a signal proportional to its acceleration. By integrating this signal, and with knowledge of initial conditions, one can obtain the velocity and position of the device. Circuitry to accomplish this integration is well-known, and may be included within the housing of the monitor shown in FIG. 10, and described later. Thus, in this specification, it will be assumed that one can use accelerometers to derive information on position, velocity, and acceleration of the athlete and of the mass. In the preferred embodiment, the accelerometers transmit their data wirelessly. But the invention could also be practiced with wired connections.

Figure 8:
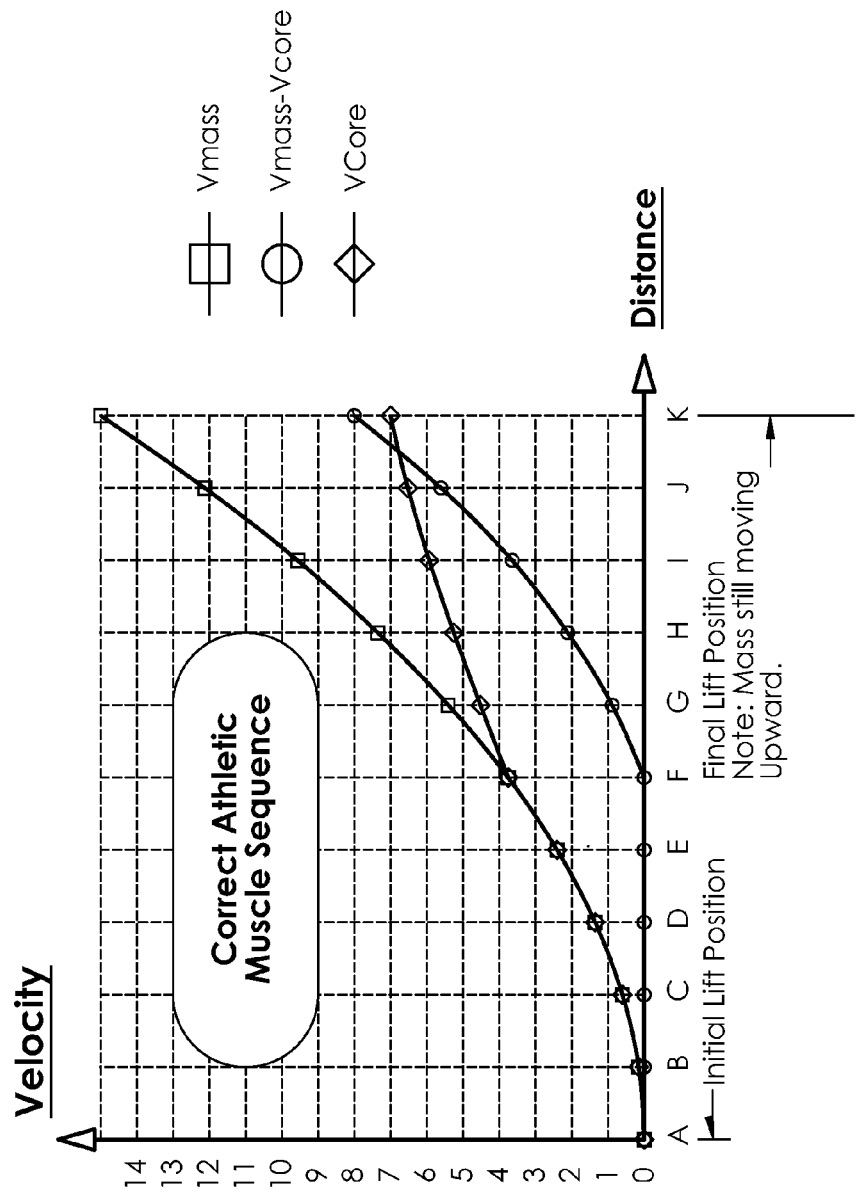
FIG. 8 provides a graph showing the correct motion of the mass, and of the athlete, when using the machine of the present invention.

FIG. 8 provides a graph which illustrates the movement of the mass, and of the athlete, when the athlete is performing the exercise correctly. In FIG. 8, $V_{mass}$ is the velocity of the mass, and $V_{core}$ is the velocity of the athlete. The term "core" is used to refer to the fact that the accelerometer is preferably placed on some central or core location on the athlete, such as on a belt attached around the athlete's waist. The vertical axis indicates velocity, and the horizontal axis indicates position. The positions shown on the graph range from the initial lift position to the position at which the athlete releases the mass, and the mass continues to move upward with no further help from the athlete.

Instead of being placed on the athlete's waist, the accelerometer could instead be mounted to a component which moves with the athlete, such as a seat, in cases where there is a sliding seat.

In FIG. 8, there is a third plot, namely $V_{mass}$-$V_{core}$, which is the difference between the velocity of the mass and the velocity of the athlete.

Figure 9:
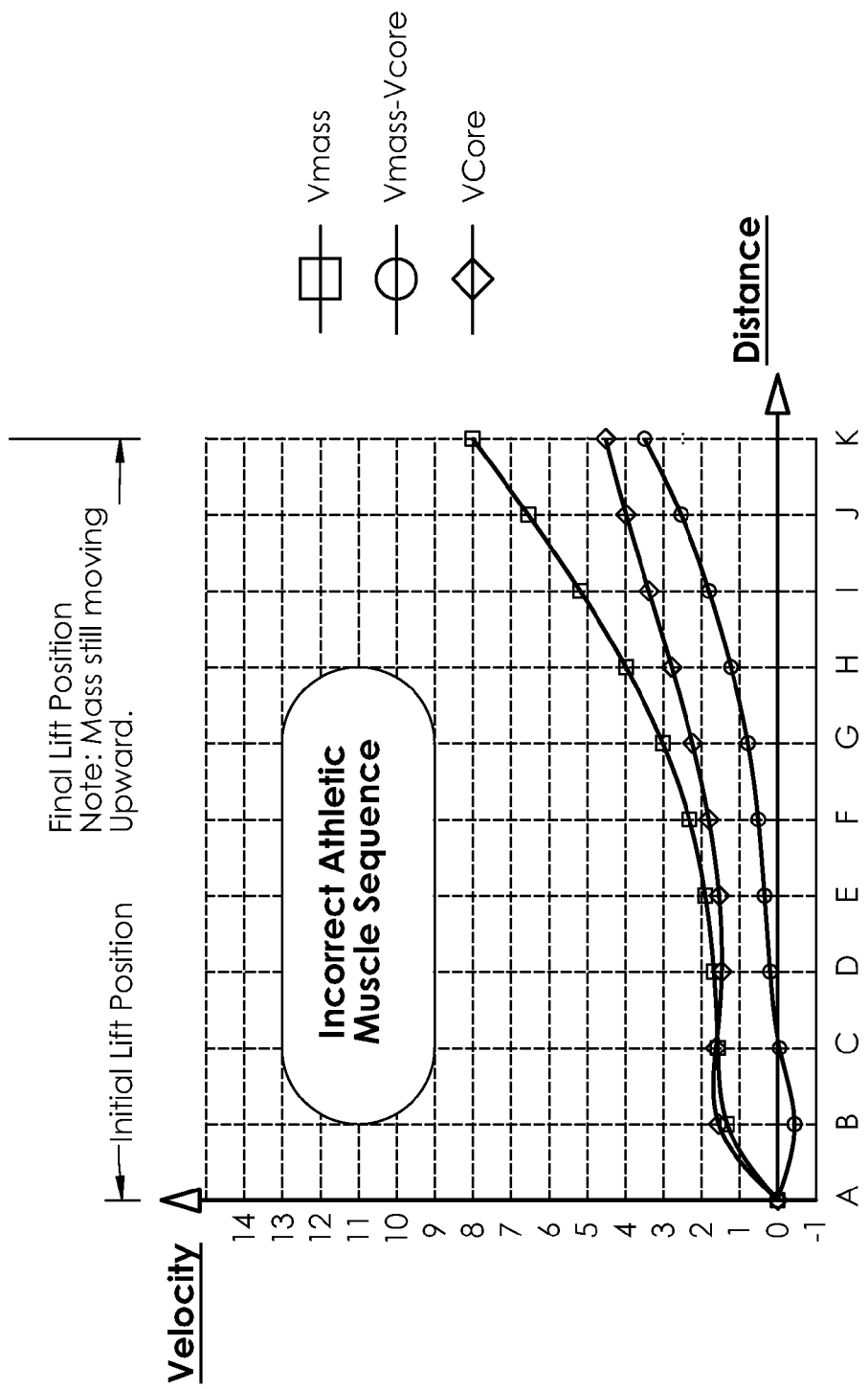
FIG. 9 provides a graph showing hypothetical undesirable motions of the mass, and of the athlete, when using the machine of the present invention.

FIG. 9 provides a graph similar to that of FIG. 8, but in which the athlete has not performed the exercise in an optimal manner. In FIG. 9, it is apparent that $V_{core}$ has a local maximum, in the vicinity of points B and C. This local maximum indicates that the athlete has initiated the use of certain small muscle groups too early. In an ideal situation, as represented by FIG. 8, there are no local maxima.

Also, in FIG. 9, the plot of $V_{mass}$-$V_{core}$ decreases at point B, before resuming its increase. The plot here indicates that the athlete is working against the small muscle groups. This plot should be monotonically increasing, as is true in FIG. 8, and should not have any dips.

Thus, to the extent that the exercise profile of an athlete resembles the graphs of FIG. 8, the athlete can be judged to be performing the exercise correctly. But if the profile contains some or all of the features illustrated in FIG. 9, the performance can be judged flawed.

Another criterion for judging the performance of the athlete is called the Drive Ratio. The Drive Ratio is defined as Time to $X_{max}$/(Time to half-$X_{max}$)

The quantity $X_{max}$ is the maximum distance traversed by the mass. Thus, the Drive Ratio is the ratio of the time required for the mass to reach $X_{max}$, to the time required for the mass to reach a point which is halfway to its maximum distance. When the athlete is performing the exercise well, the acceleration of the mass will be very great, and the first half of the stroke will cover most of the distance of the stroke. In the ideal case, the Drive Ratio will tend towards a limit of one, and in practice, its value will typically be between one and two. Therefore, the performance of the athlete is considered best when the Drive Ratio is as close to one as possible. The system can be programmed to display this ratio for each stroke of the exercise.

Still another criterion for judging the performance of the athlete is called the Core Departure Point. In brief, this criterion measures the extent to which the athlete wastes motion by moving his or her body before causing the mass to move. In particular, the system is programmed to display $X_{mass}$, i.e. the position of the mass, at the first occurrence of the relationship $V_{core}=V_{mass}*0.99$. That is, the system records the first moment at which the velocity of the core, i.e. the velocity of the athlete, is slightly less than the velocity of the mass. The value $V_{core}$ can be calculated by multiplying the measured acceleration, from the accelerometer, by time.

Thus, the system will display $X_{mass}$ at the moment when the velocities described above start to become unequal. This display occurs once for each stroke of the exercise. The object of the athlete is to try to maintain a desired number, over a series of strokes of the exercise. The desired number can be chosen by a coach, or by the athlete. The figure 0.99 is inserted to remove noise from the measurement, and could be changed. The value of 0.99 is an assumed margin of noise.

Figure 10:
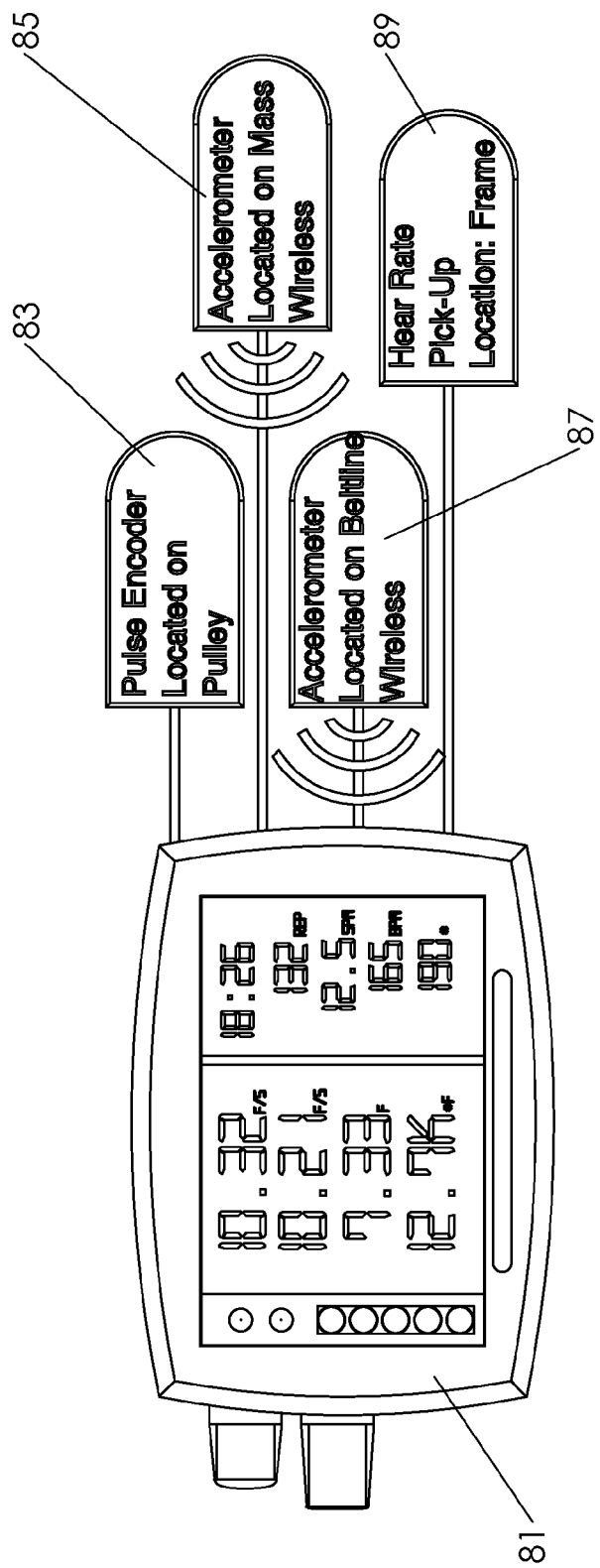
FIG. 10 provides a diagram of a monitor and sensor system, used in conjunction with the exercise machine of the present invention.

FIG. 10 illustrates the monitor, and associated components, used in the present invention. Monitor 81 may include the computer which processes data from the various sensors, and may include a display as shown. The display may include information on position, velocity, and/or acceleration of the mass and/or the athlete. The monitor is connected to a pulse encoder 83 which is located on one of the pulleys at the top of the exercise machine. The purpose of the encoder is to provide an alternative means for sensing the movements of the mass, when the accelerometer is not working, or when wireless technology is not permitted or available. The accelerometers are indicated by reference numerals 85 and 87, and include the device attached to the mass as well as the device attached to the athlete. A heart-rate pick-up 89 can also be provided, enabling the monitor to display the athlete's heart rate, if desired.

The monitor can also be programmed to display advice to the athlete on whether the exercise is being performed correctly. That is, the system generates graphs similar to those shown in FIGS. 8 and 9, and if the undesirable features (such as local maxima or dips in the curve) are found, the system can so alert the athlete. The athlete receives such advisories in real-time, and can attempt to modify his or her performance, on the next cycle, so as not to receive the same advisory. In this way, the present invention provides immediate feedback to the athlete, and enhances the ability of the athlete to improve on his or her performance.

Figure 11:
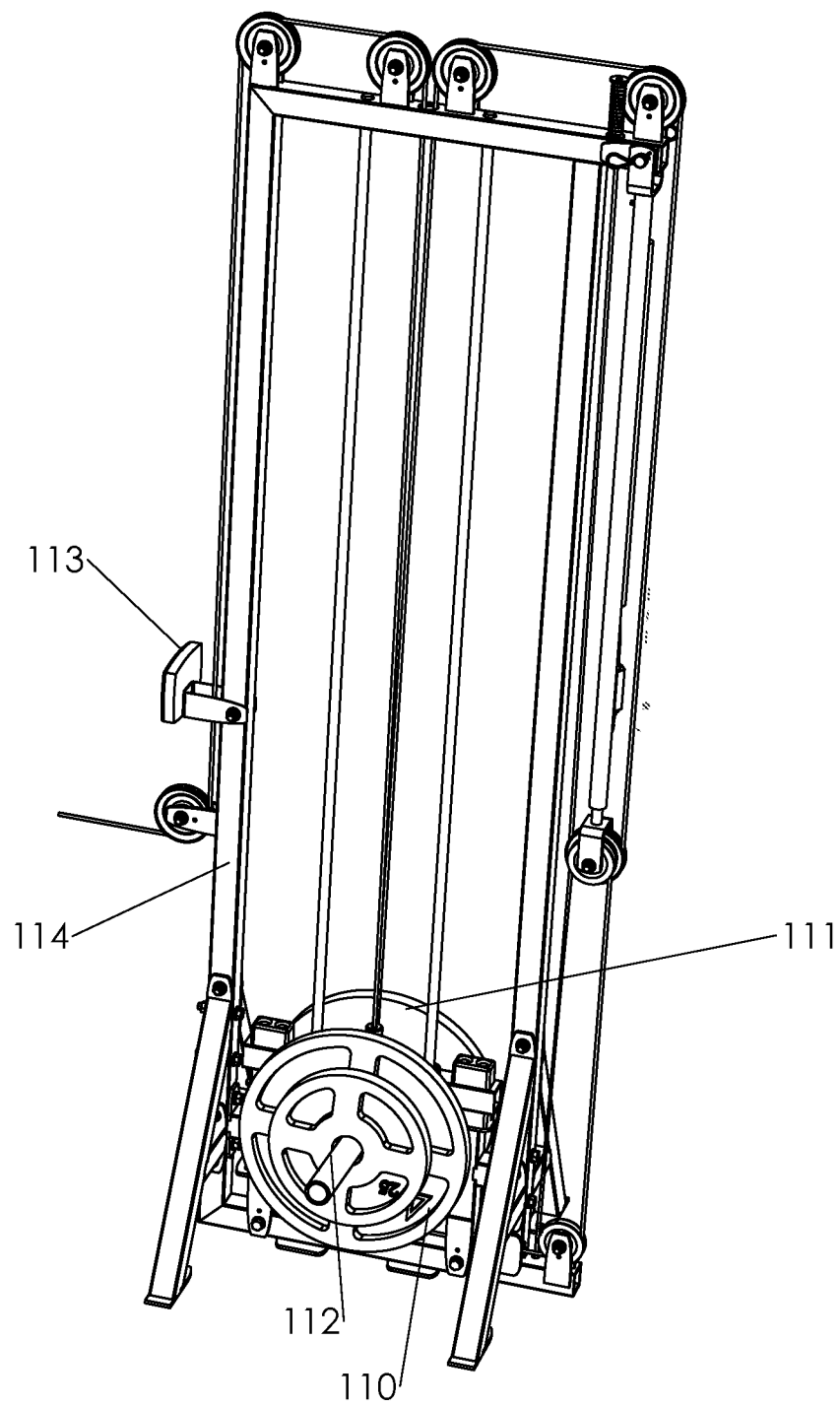
FIG. 11 provides a perspective view of a particular practical embodiment of the present invention.

FIG. 11 provides a perspective view of a practical embodiment of the exercise machine of the present invention. In FIG. 11, the mass takes the form of a pair of spaced-apart wheels 110 and 111, mounted on axle 112. A monitor 113 is mounted to frame 114 to allow the athlete to view the progress of the exercise. The other components, including pulleys, cords, tracks, and the piston and cylinder assembly, are substantially the same as described with respect to FIG. 1.

Figure 12:
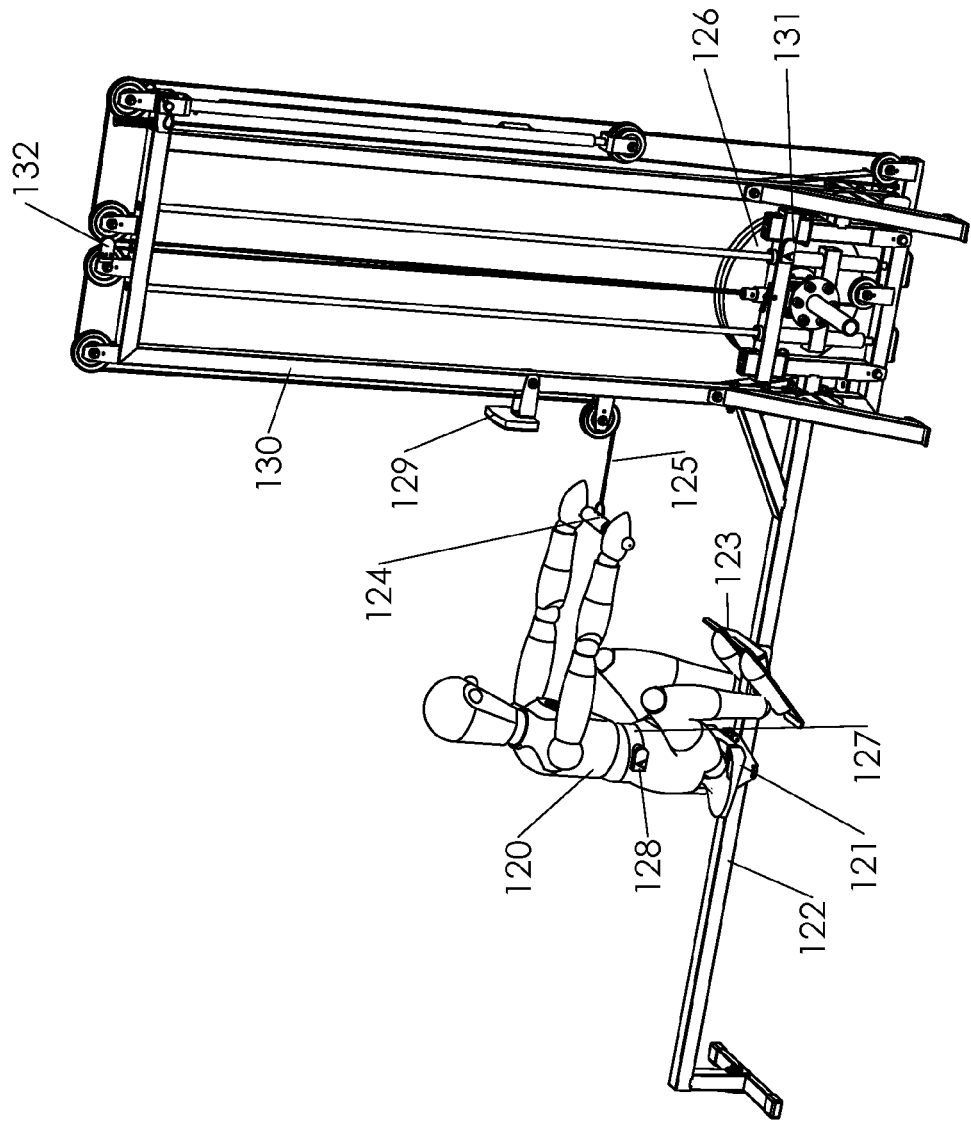
FIG. 12 provides a perspective view of another embodiment of the present invention, in which the exercise machine is used to provide a rowing exercise, the figure also illustrating an athlete with the sensors needed to monitor the progress of the exercise.

FIG. 12 provides a perspective view of another embodiment of the present invention, in which the exercise machine is adapted to provide a rowing exercise. The user or athlete 120 sits on a seat 121 supported by track 122. The track 122 also supports a foot rest 123. The athlete grips handle 124 which is connected to cord 125. The athlete accelerates the mass 126 through the rowing stroke. One wheel of the mass has been removed, in the view of FIG. 12, in order to make other components visible, for purposes of illustration. The machine is otherwise the same as shown in FIG. 1; the cylinder returns the mass to its starting point in the same manner described above.

FIG. 12 also shows that the athlete is wearing a belt 127 to which there is attached accelerometer 128. The accelerometer is the same as the device described above, which preferably wirelessly transmits information on position, velocity, and acceleration, to a computer or equivalent device. The computer could be included in the same housing has that of monitor 129, which is attached to the frame 130 of the exercise machine, or it could be housed separately.

The athlete may also wear a heart rate monitor (not shown), so that the display device can include the heart rate data as suggested in FIG. 10.

In one embodiment, the seat can be fixed on track 122. In another embodiment, the seat could be constructed so that it can slide along the track. The accelerometer could alternatively be located on the seat, in the arrangement wherein the seat moves relative to the track.

Accelerometer 131 is mounted to the mass, so as to provide the information on movement of the mass, as described above.

Rotary encoder 132 is attached to one of the pulleys at the top of the machine. The encoder is used to measure the velocity and acceleration of the mass, in cases where wireless transmission is not available, and/or where the accelerometer has failed.

It should be understood that, while the accelerometers, on the athlete and on the mass, are explicitly shown only in FIG. 12, such components are applicable to all of the other embodiments of the present invention.

Figure 13:
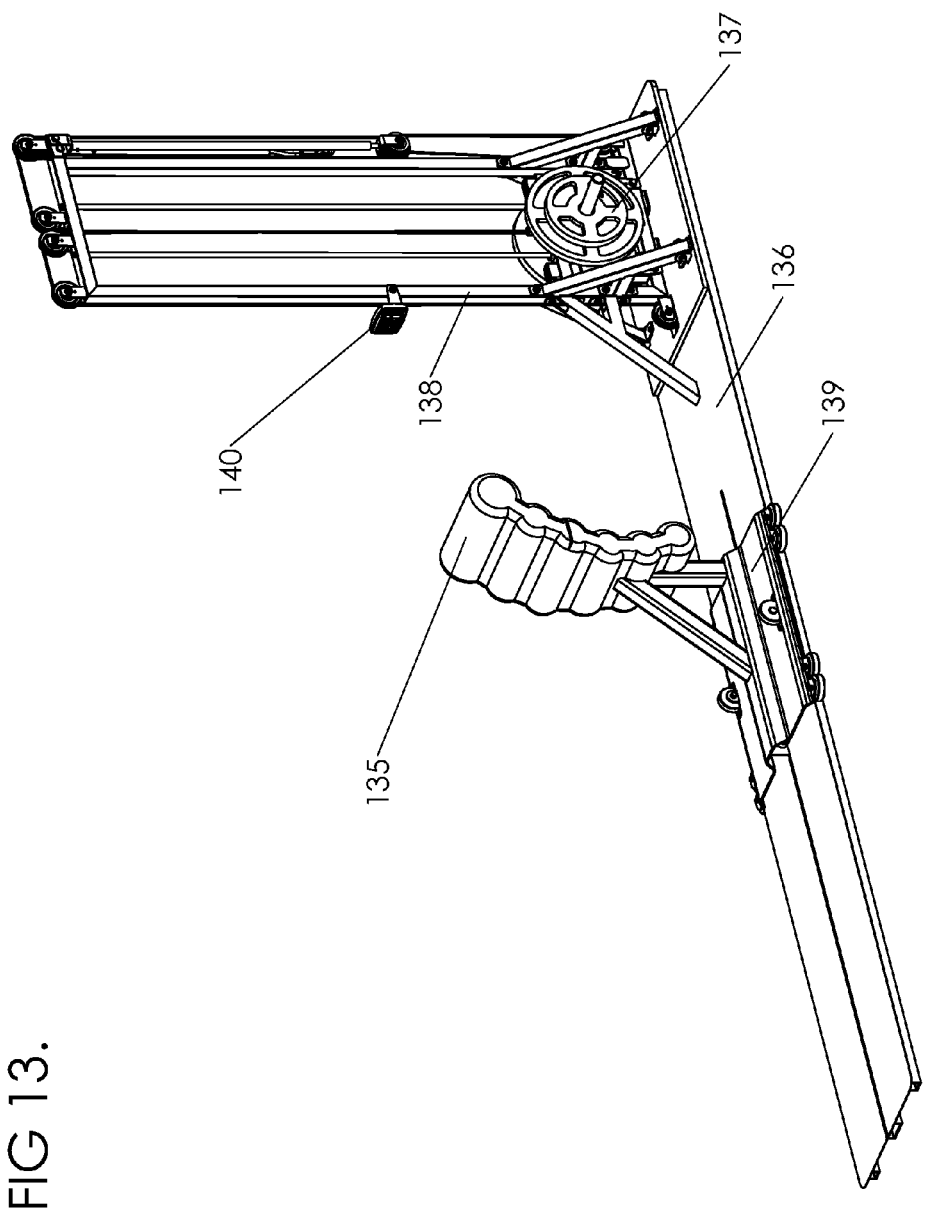
FIG. 13 provides a perspective view of another embodiment of the present invention, in which the exercise machine is used for training in football.

FIG. 13 provides a perspective view of an embodiment of the present invention, intended for use in football training. In this arrangement, the user starts in a "football" stance, and drives a blocking pad 135 linearly, along track 136. In so doing, the user lifts the mass 137 of the exercise machine. A cord 138, which lifts the mass, is connected to a carriage 139 on which the blocking pad is mounted, the cord extending under the track and not being fully visible in FIG. 13. The machine is otherwise the same as described with respect to FIG. 1. The athlete lifts the mass, and the cylinder cushions the fall of the mass to its starting point. The monitor 140 computes data relative to the exercise, and displays information to the athlete, as previously described.

Figure 14:
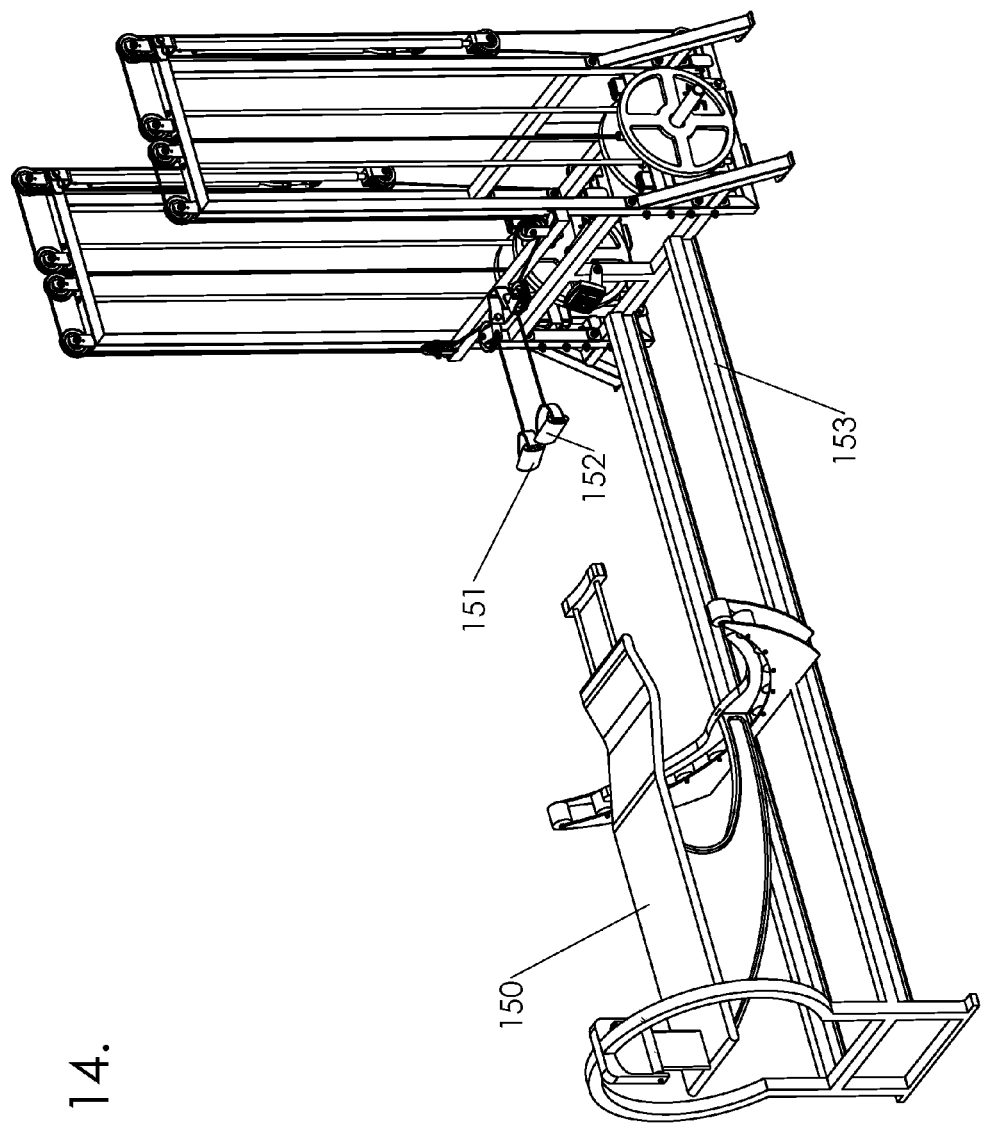
FIG. 14 provides a perspective view of another embodiment of the present invention, in which the exercise machine is used for training in swimming.

FIG. 14 provides a perspective view of an embodiment which provides a swimming exercise. The user rests on board 150 in a freestyle swimming position. The board is supported by track 153. The athlete holds grips 151 and 152, and accelerates them to simulate a swimming motion. In this embodiment, there are two exercise machines, each substantially identical to that of FIG. 1 or 11, each grip being connected to a cord that lifts the mass of the respective machine. The machines work in the same way as described above. It is preferable to provide a single monitor, which can process and display data relating to the movements of the masses of both machines.

Figure 15:
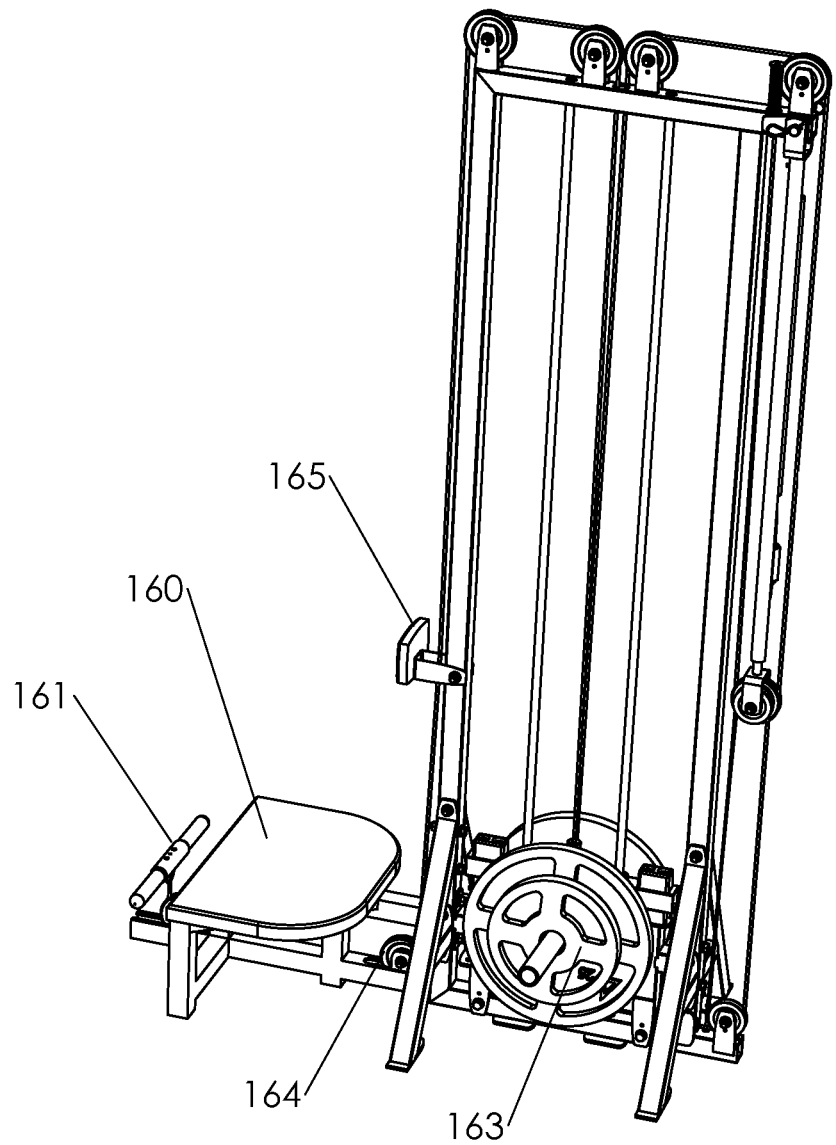
FIG. 15 provides a perspective view of another embodiment of the present invention, in which the exercise machine is used for training in lifting a weight from a squatting position.

FIG. 15 provides a perspective view of another embodiment, in which the user stands on platform 160, and directly grasps handle 161 associated with mass 163. The athlete grips the handle while in a squatting position, and accelerates the handle upward to eye level. A cord, which is partly obscured in the view of FIG. 15, is connected to the handle, and passes around a pulley near the handle (which pulley is mostly obscured in the figure), then around pulley 164, and then towards the top of the machine as described previously. The cylinder and piston cushion the return of the mass to the starting point. Monitor 165 measures the parameters of the mass and of the athlete, and provides a display of information as described above.

Figure 16:
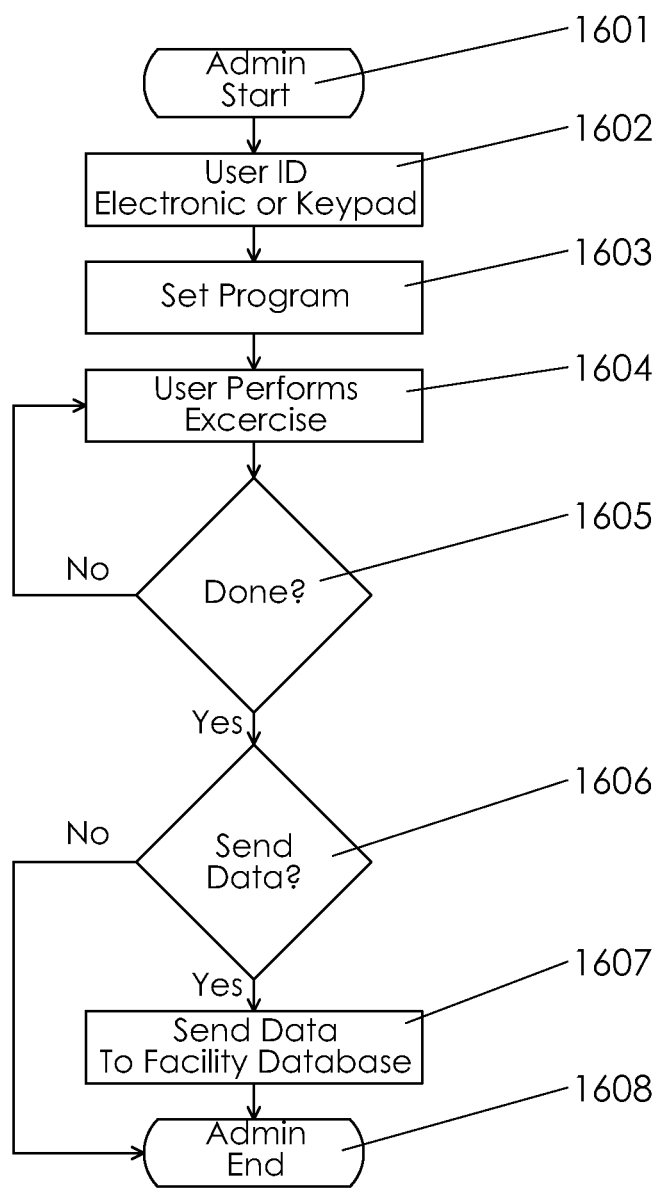
FIG. 16 provides a flow chart illustrating the functions of the software used in the present invention.

FIG. 16 provides a flow chart showing the basic functions of the software which is used with the machine of the present invention. The system is started in block 1601. The user enters an identification code, and this input is received in block 1602. In block 1603, the user selects the exercise to be performed. This selection could also include an input which indicates the number of repetitions the athlete wishes to do. More details about the functions of this block are provided later. In block 1604, the user performs the exercise. Test 1605 determines whether the exercise is finished, i.e. whether the user has performed a desired number of repetitions. When the exercise is finished, the system asks the user to confirm that the data from the exercise should be sent to a central database. Test 1606 detects the answer given by the user, and if the user has so indicated, the data are sent to the database in block 1607. The program ends in block 1608.

Figure 17:
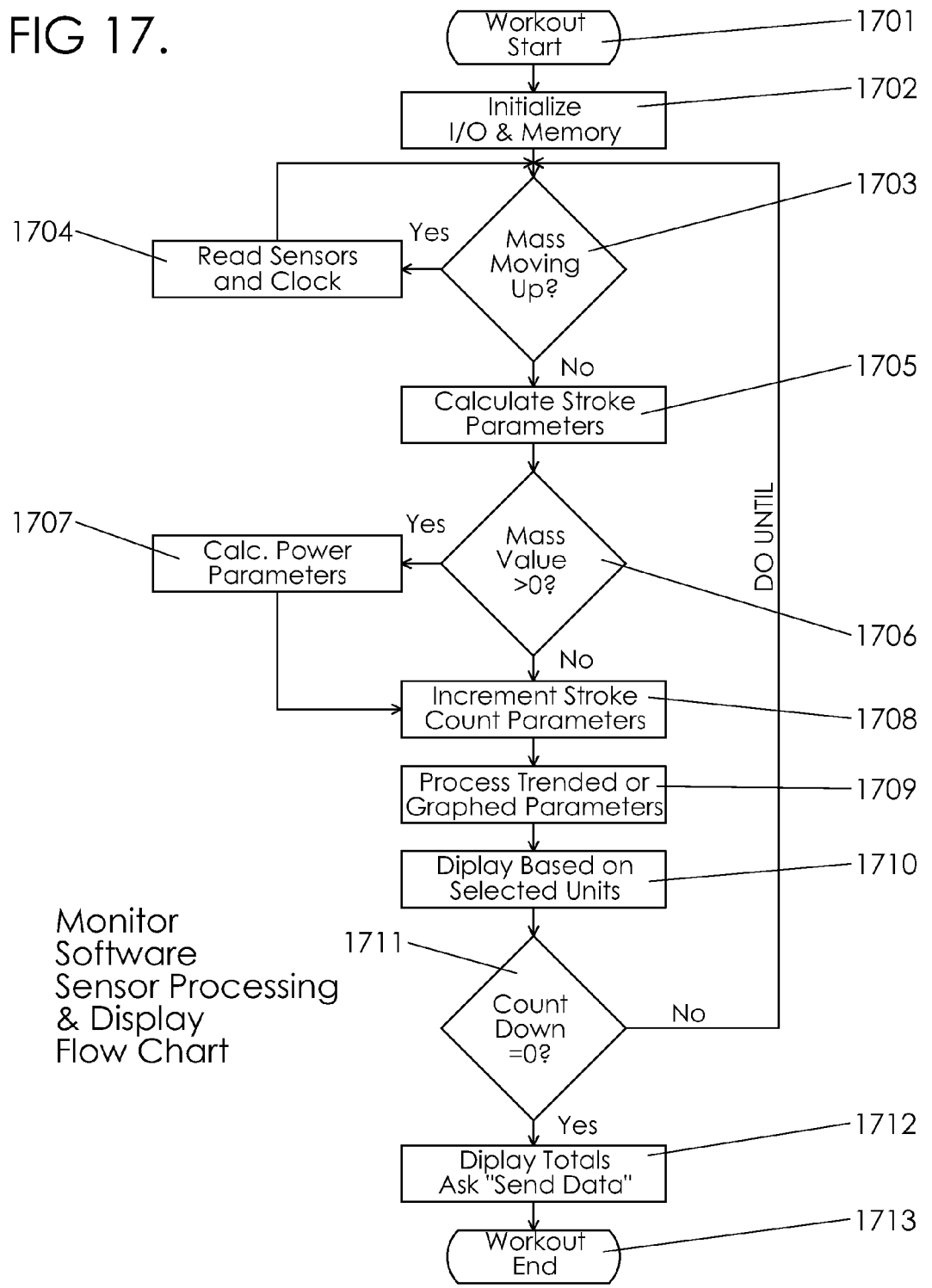
FIG. 17 provides another flow chart, illustrating the functions of the software used to conduct an exercise, according to the present invention.

FIG. 17 provides a flow chart illustrating the programming of the computer with regard to a particular exercise. Thus, the flow chart of FIG. 17 shows what occurs during execution of block 1604 of FIG. 16.

The workout starts in block 1701. The system initializes the input/output channels and memory, in block 1702. If the mass is moving upward, as determined by test 1703, the system reads data from the sensors and a clock, in block 1704. When the mass is no longer moving upward, the system calculates various parameters associated with the exercise, in block 1705. Such parameters may include maximum speed of the mass, maximum height of the mass, velocity of the mass, the stroke rate, etc. A list of parameters is given in FIG. 19, and will be described later.

Before beginning the exercise, the user should input a value for the weight of the mass. But in the event that the user has failed to do so, test 1706 insures that the system does not attempt to divide by zero. If the weight of the mass is non-zero, the system calculates various power parameters, in block 1707. These power parameters will be described later.

The system increments stroke count parameters in block 1708. In other words, the system updates a count to determine what stroke the athlete has just performed, or updates a value of another parameter that is "accumulated", i.e. for which a running total is computed. The parameters which are accumulated are listed in the table of FIG. 19, to be described later. In block 1709, the system processes certain parameters which are trended or graphed, as will be described later.

In block 1710, the system displays information to the user. In general, each separate exercise program may have a different choice of data which may be displayed. In general, the display will show the values that are incrementing, based on the program selected. A countdown program would show the value being counted down. Other parameter display features can be made options selectable by the user. The user could select a graphical display where the vertical axis is the parameter, and the horizontal axis would be the stroke for trended values. The user could also select a graphical display where different parameters appear on the horizontal and vertical axes.

The system counts the number of strokes, and determines, in test 1711, whether the number of remaining desired strokes has reached zero. If not, the system repeats the exercise cycle. If the number of desired remaining strokes is zero, the user has finished the exercise, and the system displays data to the user, and asks the user whether the data should be sent to a central database. This function is what is detected by test 1606 of FIG. 16. The end of the workout is represented by block 1713.

Figure 18:
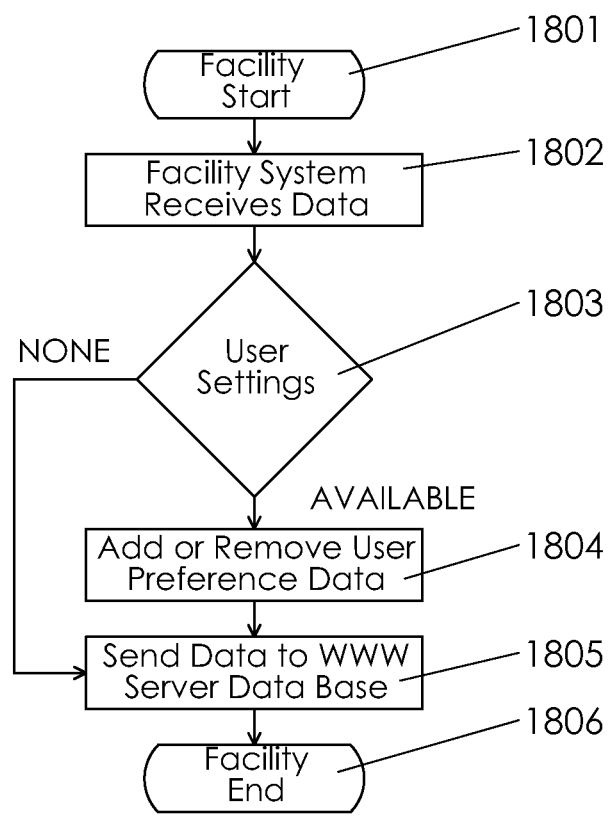
FIG. 18 provides another flow chart, illustrating the software used by a central facility, according to the present invention.

FIG. 18 provides a flow chart which describes the transfer of data to a central database. The program starts in block 1801. The data facility receives data in block 1802. These are the data from the exercise, transmitted when the user gives authorization in response to the query represented by block 1712 of FIG. 17. Test 1803 determines whether the user has indicated a desire to change personal settings. Such settings can be changed in block 1804. These settings can include, among other things, personal preferences regarding privacy. The data are sent to a web server, in block 1805. The program ends in block 1806.

Block 1603 of FIG. 16, labeled "Set Program" enables the user to set various parameters relating to the exercise to be performed. The following is a list of possible parameters which may be set. Multiple entries for the same descriptor indicate alternative choices:

1. Set count of repetitions—the program will count down from a Set Count until the count reaches zero.
2. Set count of repetitions—the program will count lift repetitions from zero until the count reaches a predetermined limit.
3. Set distance of lifts—each lift $X_{max}$ is accumulated until a Set Distance is reached.
4. Set distance of lifts—each lift $X_{max}$ is decremented from a Set Distance until zero is reached.
5. Set time—the program clock counts down from a Set Time until zero is reached.
6. Set time—the program clock counts up from zero until a Set Time is reached.
7. Set Count/Set Height—the program counts only the strokes that go above a Set Height point, until a Set Count is reached.
8. Set Lift Target/Set Weight Used—the program accumulates the weight used times $X_{max}$×Repetitions, until a target lift is reached. For example, 300 pounds used, each lifted about five feet, with 200 repetitions yields 300,000 ft lbs. The program monitors this procedure.

FIG. 19 provides a table which describes the various stroke parameters referenced in block 1705 of FIG. 17. The system can calculate any or all of the parameters mentioned in the figure. The columns labeled "accumulated" and "trended-graphed" refer to the fact that some parameters are accumulated, i.e. a running total is kept, and some parameters are graphed or analyzed for trends. In the table, the symbol "A" means acceleration. Thus, for example, the parameter $X_{drive}$ represents the height of the mass when acceleration is zero.

The power parameters mentioned in block 1707 of FIG. 17 are as follows. The first parameter is Work, defined as the work expended during the lifting of the mass. It is calculated as $X_{max}$×weight. This parameter is accumulated, and may be trended or graphed. The second parameter is $P_{max}$, which is the peak power exerted by the athlete. This parameter is calculated as $A_{max}$×weight, i.e. the maximum acceleration times the weight. This parameter is not accumulated, but may be trended or graphed.

The lifting mass system of the present invention is intended to be used on a wide spectrum of exercise machines. There are innumerable configurations of lifting equipment designed for specific muscle development as well as sports specific exercises, the above-described embodiments showing only a few examples thereof. The present invention complements existing exercise machines by allowing the user to accelerate the mass and record the parameters of motion instead of pressing the mass and then returning the mass to the original point.

In FIG. 1, the mass is represented as a unitary block. In practice, the mass may include stacks of weights. That is, the user may select the number of weights to be stacked together, so as to define a desired weight to be lifted. All of the embodiments of the present invention can include such selectable stacks of weights.

The present invention may include a plurality of machines, possibly located in different places, each machine including means for sending data to a central database. The central database could be Internet-based, so that the data from a plurality of athletes could be collated and displayed on a web server, for viewing and analysis by the athletes and others, such as coaches and doctors. Such databases could also be useful in keeping performance records, and in conducting research on the performance of various athletes.

The invention can be modified in various ways, as will be apparent to the reader skilled in the art. As described above, there are many applications in which the invention is useful. Additional applications, not explicitly described above, could be used with the present invention. Also, the specific means of providing damping need not be a piston and cylinder assembly, but could be some other damping means instead. These modifications should be considered within the spirit and scope of the following claims.

What is claimed is:

1. A method of monitoring and analyzing performance of an athlete, comprising:
   a) providing an exercise machine in which an athlete repeatedly exerts force so as to lift a mass, wherein the machine includes damping means for cushioning a fall of the mass to a starting position,
   b) obtaining position data from a first sensor representative of movement of the athlete,
   c) obtaining position data from a second sensor attached to the mass, and
   d) analyzing data from said first and second sensors so as to evaluate performance of the athlete,
   further comprising using data from said sensors to derive graphs representing a velocity of the mass ($V_{mass}$) and a velocity of the athlete ($V_{core}$), determining whether such graphs include a condition indicative of incorrect performance of an exercise, and signalling presence of such condition to the athlete.

2. The method of claim 1, wherein the first sensor is located on a belt attached to the athlete.

3. The method of claim 1, wherein the first sensor is located on a component of the exercise machine which moves with the athlete.

4. The method of claim 1, wherein said condition is selected from the group consisting of the presence of a local maximum in $V_{core}$, and failure of $V_{mass}$-$V_{core}$ to increase monotonically.

5. A method of monitoring and analyzing performance of an athlete, comprising:
   a) providing an exercise machine in which an athlete repeatedly exerts force so as to lift a mass, wherein the machine includes damping means for cushioning a fall of the mass to a starting position,
   b) obtaining position data from a first sensor representative of movement of the athlete,
   c) obtaining position data from a second sensor attached to the mass, and
   d) analyzing data from said first and second sensors so as to evaluate performance of the athlete,
   further comprising using data from said sensors to measure a time required for the mass to reach a maximum distance, and computing, for each performance of an exercise, a Drive Ratio defined as a time required for the mass to reach a maximum distance, divided by a time required for the mass to reach halfway to its maximum distance, and displaying the Drive Ratio.

6. A method of monitoring and analyzing performance of an athlete, comprising:
   a) providing an exercise machine in which an athlete repeatedly exerts force so as to lift a mass, wherein the machine includes damping means for cushioning a fall of the mass to a starting position,
   b) obtaining position data from a first sensor representative of movement of the athlete,
   c) obtaining position data from a second sensor attached to the mass, and
   d) analyzing data from said first and second sensors so as to evaluate performance of the athlete,
   further comprising using data from said sensors to measure velocities of the athlete and the mass, and computing and displaying a position of the mass at a time when a velocity of the athlete falls below a velocity of the mass.

* * * * *